(12) United States Patent
Wertheim et al.

(10) Patent No.: US 7,204,591 B2
(45) Date of Patent: Apr. 17, 2007

(54) DEVICE USING LIGHT EMITTING DIODES FOR PREDICTING THE OPTICAL DENSITY AND DIAGNOSTIC COLOR OF SUNGLASS OR THERAPEUTIC LENSES USING CONTRAST SENSITIVITY INFORMATION

(76) Inventors: Herbert A. Wertheim, 4470 SW. 74th Ave., Miami, FL (US) 33155; William F. Moore, 4470 SW. 74th Ave., Miami, FL (US) 33155; Philip R. Bartick, 4470 SW. 74th Ave., Miami, FL (US) 33155

( * ) Notice: Subject to any disclaimer, the term of this patent is extended or adjusted under 35 U.S.C. 154(b) by 344 days.

(21) Appl. No.: 10/805,587

(22) Filed: Mar. 22, 2004

(65) Prior Publication Data

US 2005/0213038 A1   Sep. 29, 2005

(51) Int. Cl.
*A61B 3/02*   (2006.01)

(52) U.S. Cl. .......................... 351/223; 351/222
(58) Field of Classification Search ............... 351/213, 351/222, 223
See application file for complete search history.

(56) References Cited

U.S. PATENT DOCUMENTS

| | | | |
|---|---|---|---|
| 4,405,216 A | 9/1983 | Nadler | |
| 4,764,007 A | 8/1988 | Task | |
| 4,784,483 A * | 11/1988 | Holladay et al. | ........... 351/243 |
| 5,007,730 A | 4/1991 | McAllister | |
| 5,671,039 A | 9/1997 | Grolman | |
| 5,774,202 A * | 6/1998 | Abraham et al. | ........... 351/177 |
| 5,886,770 A * | 3/1999 | Damato | ...................... 351/237 |
| 6,099,126 A | 8/2000 | Teskey | |
| 6,585,377 B2 | 7/2003 | Ortega | |

* cited by examiner

*Primary Examiner*—Scott J. Sugarman

(57) ABSTRACT

A device using light emitting diodes directed at the patient as a light source for evaluating the appropriate color and density of filters or sunglasses for a patient is disclosed. The device may be used with additional filters or sunglasses to determine what filter or sunglass color and density will provide optimal vision for targets of varying spatial frequency. The device may also be used with additional filters of varying color and density to determine the health of the patient's ocular media.

3 Claims, 1 Drawing Sheet

Figure 1:
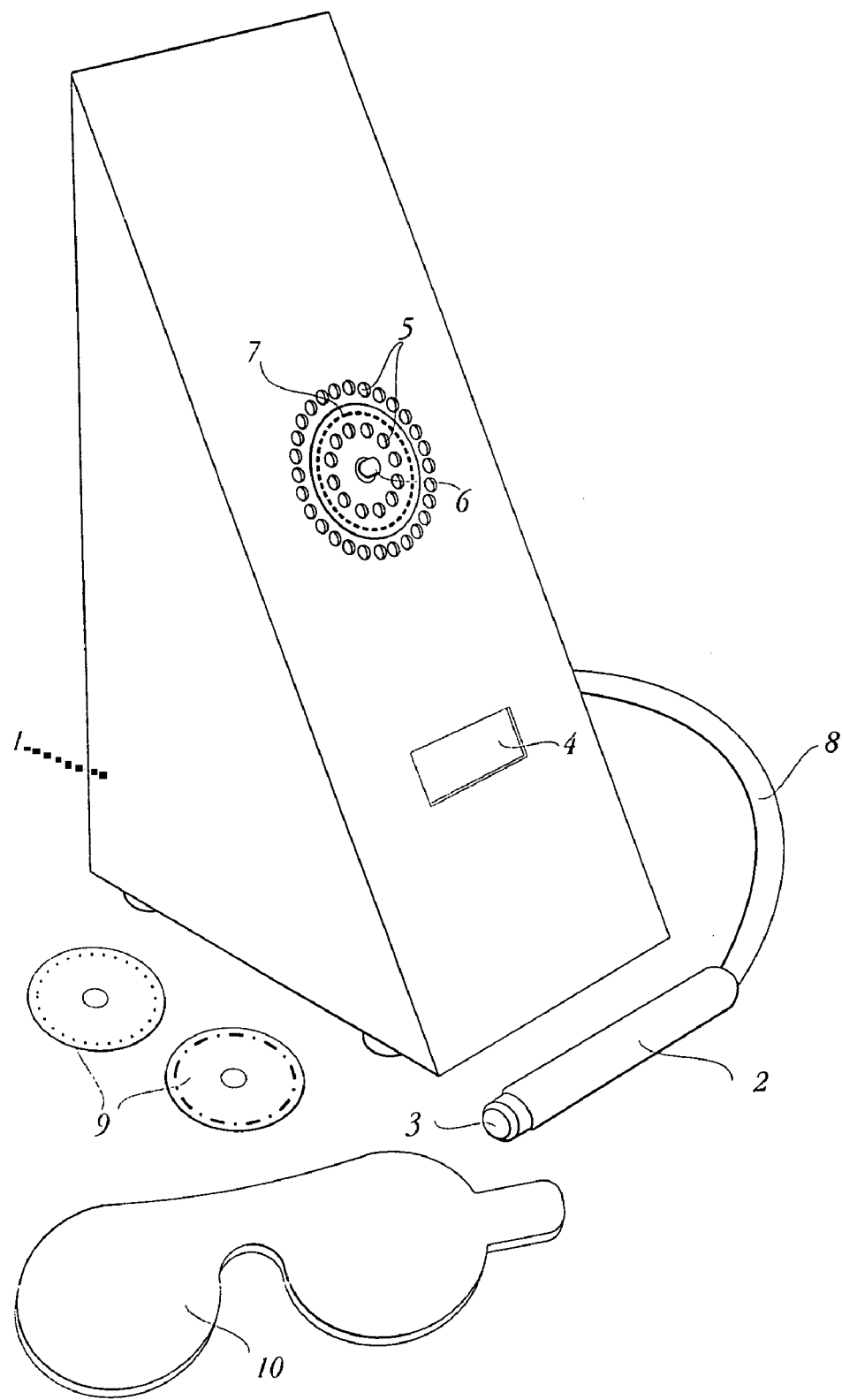

DEVICE USING LIGHT EMITTING DIODES FOR PREDICTING THE OPTICAL DENSITY AND DIAGNOSTIC COLOR OF SUNGLASS OR THERAPEUTIC LENSES USING CONTRAST SENSITIVITY INFORMATION

BACKGROUND

1. Field of the Invention

The invention relates to a device used to determine the optical density and color of sunglass or therapeutic tints required for the comfort and optimal visual performance of the person being tested. The device also has been designed for checking the overall condition of the retina, cornea, macula and crystalline lens as regards macular degeneration and color and contrast sensitivity. The device may also find application in detecting retinal integrity as well as cataracts in the crystalline lens and other ocular media. Sunglass lenses and other filtering lenses have been used for centuries, however the determination regarding what sunglass optical filter density and color would be appropriate for a given patient has been left almost entirely to the subjective judgment of the patient and dispenser. Ophthalmic determination of a proper sunglass optical filter density for a patient has only been attempted with bright incandescent lights as the source of high intensity light. This device uses white light emitting diodes to produce a bright light in the vicinity of a specially constructed pattern, enabling the practitioner to determine the required density and color by discovering the lighting conditions required to obscure the particular pattern seen by the patient. It has been determined in studies (Paul de Land, 2000) that contrast sensitivity is dependent on pattern spatial frequency and is altered by the presence of intervening filters of various optical densities and colors. This test, by using patterns with various different spatial frequencies, can potentially be used to determine the required optical filter density and color for the patient to safely detect important patterns such as traffic warning signs. Additionally, such testing may also reveal early stages of macular degeneracy and cataracts of the crystalline lens and other ocular media.

2. Description of Prior Art

Devices similar to this unit are the Brain Power Incorporated Sun Glass Doctor and Solar Sensitivity Meter. These units employ bright incandescent bulbs to supply the bright light used to determine the sunglass density and color level required for specific patients. Sunglasses have been used for centuries and their optical densities in the visible portion of the spectrum have been routinely checked. Determination of the proper density appropriate to the patient using this contrast sensitivity type of test has been attempted by the BPI units previously mentioned. Patients have been evaluated by glare testing in order to obtain related information. Task describes a device wherein light glares through a transparent panel upon which a pattern is placed. McAllister, et al. describe a similar device wherein the glaring light passes through a transparent opening with an opaque pattern surrounding it. Grolman describes a ring of light emitting diodes surrounding a central axis through which the patient attempts to perceive a pattern. The pattern is illuminated and caused to be obscured by the glare of the LED's; the LED's are pointed away from the patient, toward the pattern. Teskey describes a sunlight sensitivity tester wherein a computer controlled illuminated screen provides a test pattern. The screen is then illuminated with a variety of illuminating sources directed at the viewing screen. Filters may be placed between the patient and the viewing screen. Nadler describes an opaque target surrounded by a translucent ring which allows glaring light from an incandescent lamp to pass through, directed at the patient. Ortega, et al., describe a pattern of lit dots surrounding a luminous central glare region.

Objects and Advantages

The device being discussed differs from all such similar devices by the use of light emitting diodes as the source of high intensity light directed at the patient. Focused light emitting diodes are especially useful in this embodiment of the device since the power requirements are further reduced by directing light only at the patient. This power reduction along with the intrinsic power reduction from using light emitting diodes in place of an incandescent bulb leads to a lower operating temperature for the unit and a longer life time for all associated parts. Furthermore, the power line noise produced by modulating the light intensity of a high power incandescent bulb is eliminated by using the light emitting diodes. The light intensity of the diodes is varied by either adjusting the current flowing to them or by time domain modulating that small current using pulse width modulation. The latter technique is the preferred embodiment since the micro-controller which controls the operation of the device easily provides the needed modulating signal. The modulating frequency and current produce a light source that is totally controllable by a computer program. This program helps to produce the variable light stimulus that is needed for spatial frequency determination to check visual function integrity. Each of the light emitting diodes can be individually controlled to produce a sweeping motion across the retina. The use of discrete light emitting diodes allows the light pattern to be shaped to best suit the application. In the preferred embodiment of this device the light emitting diodes are configured in two concentric rings with an overlay containing a target with two opaque, broken, concentric rings nested between the two diode rings as shown in FIG. 1. The target lies against the face plate of the device, which is angled in such a way as to hold the plane of the target perpendicular to the line-of-sight from the patient to the target. Typically, white light emitting diodes with light outputs of several candela are employed in this device and their light is focused toward the patient. Furthermore, this device is not shrouded or covered in such a way as to restrict the patient's peripheral visual field, thus allowing the patient's convergent and accommodative systems to function normally during the examination.

DRAWING FIGURES

FIG. 1 shows the preferred embodiment of the device along with accessories.

REFERENCE NUMERALS IN DRAWINGS

1. The preferred embodiment of the device showing the shape of the chassis.
2. The hand grasp for the push button assembly.
3. The push button which starts and stops the ramp-up of LED intensity.
4. The display which provides information regarding LED light intensity as the test progresses.
5. The concentric rings of white light emitting diodes (LED's).
6. The flashing target LED which protrudes out of the face of the machine, providing a support for the various target patterns.

7. The clear, transparent target pattern with opaque markings of differing spatial frequencies which must be distinguished by the subject as the white light LED intensity changes.
8. The electrical cord which connects the push button assembly to the device.
9. Other patterns with different spatial frequencies and other characteristics may be employed which will provide benefit in the determination of optimum viewing conditions as well as macular and crystalline lens condition.
10. Filters of various colors and densities may be placed between the device and the patient.

Description

The device consists of a chassis, 1, on which the circuit board containing the light emitting diodes, 5 and 6, is affixed, along with the computer board and the display board (not shown—inside the device). Power for the unit can be supplied by an internal power supply, external power pack or batteries. The light emitting diode pattern, 5 and 6, and overlay target pattern, 7, held by the chassis at an angle perpendicular to the light path from pattern to eye for the preferred embodiment are shown in FIG. 1. The device is non-shrouded so that the accommodative and convergent systems of the eye are unimpeded.

Operation

In use, the patient sits in front of the pattern of light emitting diodes, about ½ meter from the target pattern and in the direct beam of the diodes. A flashing light emitting diode, 6, located at the center of the pattern directs the patient's attention to that point. The patient is told to fixate on that point, while observing the overlay target pattern, 7, using his peripheral vision. The patient then presses a button, 3, causing the light intensity of the white light emitting diodes, 5, to change. The patient is instructed to release the button, 3, when any portion of the target pattern, 7, becomes indistinct due to the illumination. When the button, 3, is released, the display, 4, numerically presents the light's intensity relative to that of diffuse reflected sunlight. Information regarding the relative illumination of the diodes may also be presented. The light intensity then returns to its starting level. The display information is used by the optical practitioner to determine the density and color of sunglass required in order to make the target pattern distinct under full sunlight conditions as well as other lighting conditions for that patient. The test may also be performed while various colored filters, 10, or sunglasses are placed between the patient and the device in order to determine the response of the patient to differing spatial frequencies while using filters or sunglasses of differing color and density. Other information regarding the health of the eye may also be obtained by performing the test described above and using filters or sunglasses of various colors and densities.

Summary, Ramifications, and Scope

This device for determining a patient's optimum filter or sunglass color and density is the first of its type to use light emitting diodes as a light source. This reduces power consumption and heat production of the device. It also enables the use of less elaborate light intensity control circuits which produce minimal electrical interference. Using patterns of various spatial frequencies in conjunction with filters and sunglasses of various colors and densities enables the practitioner to determine which filter or sunglass colors and densities provide the best vision under various lighting conditions. The use of this device with various filters and sunglasses of differing colors and densities may also allow the practitioner to detect other health problems with the ocular media.

We claim:

1. A non-shrouded device comprising:
a plurality of individually programmable light emitting diodes;
a plurality of convex lenses, each associated with a respective one of the programmable light emitting diodes;
a test pattern disposed among the programmable light emitting diodes;
wherein the light emitting diodes are programmed to focus light in a variable circular or other pattern whose diameter is such that the focused light pattern image is protected at different distances outside the macular area of the subject's retina, and such that a variable programmable brightness of each individual light emitting diode is used to determine specific points at which the subject is no longer able to accurately differentiate the test pattern;
wherein contrast sensitivity, accommodation, convergence and acuity of the subject are computed from said specific points; and
wherein the test pattern is be used to determine the an optimum sunglass or filter color and density for the subject based on said computed contrast sensitivity, accommodation, convergence and acuity.

2. An device as in claim 1 wherein:
test patterns which exhibit various spatial frequencies are used to determine the subject's end point response to spatial frequency under varying conditions of illumination color and intensity;
filters or sunglasses of varying color arid density are interposed between the subject's eye and the test pattern to determine the range of color and density that will allow the subject to have maximum visual acuity, light adaptation, accommodation, convergence and pupil response;
saturation of different colors of light provides information regarding response and visual comfort for the optimum selection of tinted or special filter lenses for reading, sports. medical needs, occupational safety, driving and improved visual function for accurate comfortable vision.

3. A device as in claim 2 wherein:
tri-stimulus light emitting diodes capable of emitting red green and blue light in various amounts to render white light or variations of colors as programmed by a microprocessor for a specific test interact with filters of various colors, polarizations and densities interposed between the subject's eyes and the device to provide information regarding the health of subject's retina, light adaptive system; cornea and other ocular media by measuring colored or white light saturation and scattering over various adaptive periods.

* * * * *